(12) United States Patent
Rouw et al.

(10) Patent No.: US 7,738,948 B2
(45) Date of Patent: Jun. 15, 2010

(54) FORM PARAMETER FORECASTER FOR ANALYZING SIGNALS DISTORTED BY NOISE

(75) Inventors: Mattias Rouw, Arnhem (NL); Patrick Scholten, Zutphen (NL); Henricus W. M. De Bruyn, Arnhem (NL)

(73) Assignee: Medtronic, Inc., Minneapolis, MN (US)

( * ) Notice: Subject to any disclaimer, the term of this patent is extended or adjusted under 35 U.S.C. 154(b) by 323 days.

(21) Appl. No.: 11/554,778

(22) Filed: Oct. 31, 2006

(65) Prior Publication Data

US 2008/0103401 A1 May 1, 2008

(51) Int. Cl.
*A61B 5/04* (2006.01)
(52) U.S. Cl. .................. 600/509; 600/508; 600/515; 607/4; 607/5; 607/9
(58) Field of Classification Search ......... 128/901–902; 702/66–74; 600/508, 509, 515; 607/4, 5, 607/9; 341/143, 155
See application file for complete search history.

(56) References Cited

U.S. PATENT DOCUMENTS

| | | | |
|---|---|---|---|
| 5,284,152 A | 2/1994 | Portnuff et al. | |
| 5,379,776 A | 1/1995 | Murphy et al. | |
| 5,400,795 A | 3/1995 | Murphy et al. | |
| 5,439,483 A | 8/1995 | Duong-Van | |
| 5,549,647 A | 8/1996 | Stoop et al. | |
| 5,755,739 A * | 5/1998 | Sun et al. ............... | 607/14 |
| 5,999,853 A | 12/1999 | Stoop et al. | |
| 6,029,087 A * | 2/2000 | Wohlgemuth ............ | 607/9 |
| 6,212,428 B1 | 4/2001 | Hsu et al. | |
| 6,266,554 B1 | 7/2001 | Hsu et al. | |
| 6,275,732 B1 | 8/2001 | Hsu et al. | |
| 6,556,859 B1 | 4/2003 | Wohlgemuth et al. | |
| 6,654,637 B2 | 11/2003 | Rouw et al. | |
| 6,901,291 B2 | 5/2005 | Stoop et al. | |
| 7,076,289 B2 | 7/2006 | Sarkar et al. | |
| 2002/0019593 A1 | 2/2002 | Hsu et al. | |
| 2002/0032469 A1 | 3/2002 | Marcovecchio | |
| 2003/0050563 A1 * | 3/2003 | Suribhotla et al. ....... | 600/509 |
| 2003/0060849 A1 | 3/2003 | Hsu | |
| 2006/0161069 A1 | 7/2006 | Li | |

* cited by examiner

*Primary Examiner*—Carl H Layno
*Assistant Examiner*—Jennifer Stewart
(74) *Attorney, Agent, or Firm*—Stephen W. Bauer; Michael J. Ostrom (57) ABSTRACT

Waveform analysis is used to identify and distinguish components of a sensed input signal, such as P-wave and Far Field R-wave signal components present in a sensed cardiac signal, even when the components are so closely spaced in time that the overlap to create a distorted input signal. A set of composite waveforms are generated by superimposing waveform templates of the signal components with different time delays or degree of overlap. Form parameters for each composite waveform are derived and mapped in a multidimensional map, from which form parameter boundaries are derived. Waveform data is collected from an input signal during a sensed event time window, and form parameters for the input signal waveform are derived. An output identifying the signal component of interest (e.g., a P-wave) and its location within the sensed event time window is produced based upon the set of form parameters of the input signal waveform and the form parameter boundaries.

18 Claims, 7 Drawing Sheets

FORM PARAMETER FORECASTER FOR ANALYZING SIGNALS DISTORTED BY NOISE

BACKGROUND OF THE INVENTION

The present invention relates to digital signal processing using waveform morphology. In particular, the invention relates to processing signals, such as sensed cardiac signals distorted by cross talk or other noise, to identify a signal component of interest.

Implantable medical devices (IMD's) are used for a variety of monitoring and therapy delivery purposes. Many IMD's sense physiologic signals and provide outputs, either in the form of delivered therapy or in the form of monitored physiologic activity. For example, pacemakers and implantable cardioverter defibrillators (ICD) include electrodes (and in some cases other sensors) to sense cardiac activity. The sensed signals representing cardiac activity are processed in signal processing channels, and are used in the detection of cardiac arrhythmias and other conditions that require the delivery of therapy. The types of therapy that can be delivered include, for example, pacing pulses and cardioversion/defibrillation shocks delivered to the heart.

An IMD that is monitoring or delivering therapy to the heart must accurately process sensed signals that may contain noise, such as cross talk, that distorts the signal waveform. For example, a sensed signal from an atrial electrode will typically contain a P-wave signal representing depolarization of the atrium and a Far Field R-wave (FFRW) signal, which occurs when an atrial electrode detects an electrical signal resulting from ventricular depolarization.

The Far Field R-wave is normally an unwanted atrial sensed signal, and can be considered cross talk or noise. Various techniques have been developed in the past to distinguish between P-waves and Far Field R-waves, so that a Far Field R-wave is not erroneously identified as P-wave.

Signal processing of physiologic signals, such as signals representing cardiac activity, has generally been performed in IMDs by analog circuitry. Digital signal processing offers potential benefits that have been used in IMDs. In digital signal processing, the incoming sensed signal is converted to a digital signal at a specified rate. Sampled waveform data representing the input signal can then be processed digitally, which permits more sophisticated signal analysis and has generally been available with analog circuitry.

The Wohlgemuth et al. U.S. Pat. No. 6,556,859 describes the use of digital signal processing to classify sensed atrial signals as P-wave or Far Field R-waves, based upon form factor histograms. In this technique, there must be some time separation between the P-wave form factor histogram and the R-wave form factor histogram, so that each has a specific form or shape. Other techniques are required if there is an overlap or near overlap.

If a P-wave signal and a Far Field R-wave signal occur to close in time, the resulting atrial signal will have a waveform which is a combination of the two overlapping signal components. The sensed atrial waveform may be distorted to the extent that it does not resemble either of the two waveform components (P-wave and FFRW) that are overlapping. Digital signal processing techniques with the ability to extract and identify the waveform component of interest, such as the P-wave in an atrial sensed signal, would be advantageous.

BRIEF SUMMARY OF THE INVENTION

A signal component of interest in an input signal (e.g., a P-wave signal component of an atrial sensed signal) is identified using signal morphology of the input signal, even if the input signal waveform is distorted by the presence of noise (e.g., a superimposed Far Field R-wave signal component). A plurality of composite waveforms are generated using a first waveform template representing the signal component of interest and a second waveform template representing the noise signal component. Each composite waveform represents the first and second templates superimposed with a different relative time shift.

Form parameters are derived from each composite waveform, and a multidimensional map based upon the form factors of the composite waveforms is derived. A form parameter forecaster uses the multidimensional map to identify the signal component of interest from the input signal.

Waveform data from the input signal is collected during a sensed event time window, and form parameters are derived based upon the waveform data. An output is produced identifying the signal component of interest and its location within the time window based upon the form parameters of the input signal waveform and the mapped sets of form parameters.

DETAILED DESCRIPTION

In the following description, signal processing with a form parameter forecaster will be discussed in the context of an implantable medical device, and specifically in the context of processing of atrial sensed signals to identify a P-wave and distinguish it from a Far Field R-wave. It should be understood, however, that the use of the form parameter forecaster is applicable to other types of devices and to other types of signals.

Figure 1:
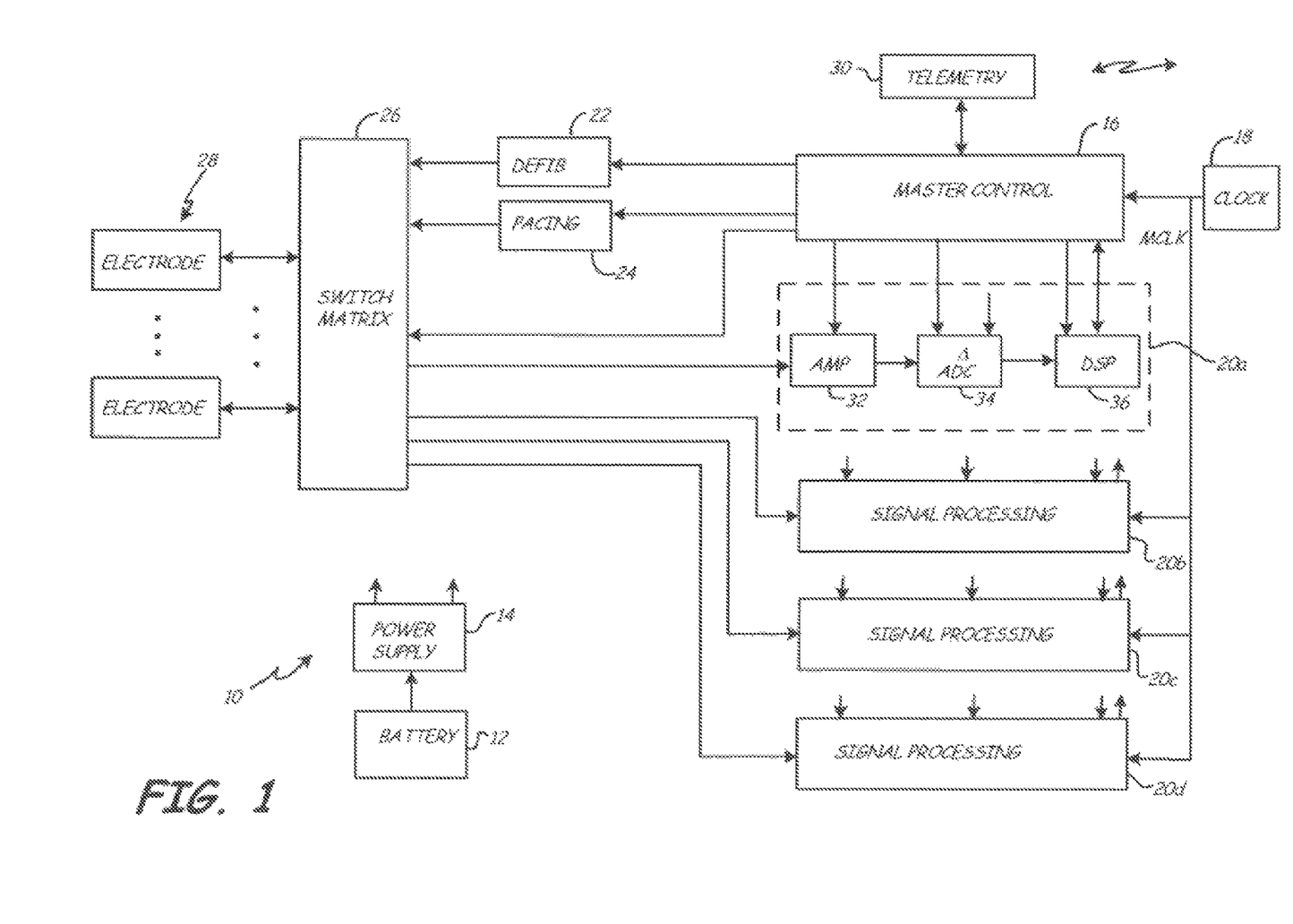
FIG. 1 is a block diagram of an implantable cardioverter defibrillator (ICD) including digital signal processing channels for processing sensed cardiac signals.

FIG. 1 is a block diagram of implantable cardioverter defibrillator (ICD) 10, which includes battery 12, power supply 14, master control 16, clock circuitry 18, signal processing channels 20a-20d, defibrillation circuitry 22, pacing circuitry 24, switch matrix 26, electrodes 28, and telemetry interface 30. Each of the signal processing channels 20a-20d is a digital signal processing channel that includes preamplifier 32, sigma-delta analog-to-digital converter (ADC) 34, and digital signal processor (DSP) 36.

Battery 12 and power supply 14 provide all of the electrical energy used by ICD 10 to perform sensing, therapy delivery, and communication with other devices. This includes supply voltages required to operate the electronic circuitry of ICD 10, and the energy required by pacing circuitry 24 to deliver pacing pulses and the voltages required by defibrillation circuitry 22 to provide cardioversion and defibrillation shocks.

Master control 16 controls the overall operation of ICD 10. It provides control inputs to each of the signal processing channels 20a-20d, determines the appropriate therapy based upon the outputs of signal processing channels 20a-20d together with stored detection criteria and therapy delivery programs, provides control signals to defibrillation circuitry 22 and pacing circuitry 24, and communicates with external devices through telemetry interface 30. Master control 16 can provide information regarding the status and operation of ICD 10 through telemetry interface 30 to an external device such as a programmer or a monitor, and may also receive downloads of information, including control settings, from an external programmer through telemetry interface 30.

Master control 16 may include, for example, a microcontroller, memory for data storage, memory for storing software and firmware, and memory for storing control settings and other information that may be provided via telemetry interface 30.

Clock circuitry 18 provides master clock (MCLK) signals to master control 16, as well as to signal processing channels 20a-20d. In the embodiment shown in FIG. 1, each signal processing channel 20a-20d derives from master clock MCLK the necessary clock signals to operate circuitry within that channel, including sigma-delta ADC 34.

Electrodes 28 may be carried by leads that extend from the housing of ICD 10 to locations in or near the heart. For example, electrodes 28 may be carried by leads that extend into the right atrium, into the right ventricle, and through the coronary sinus into a coronary vein adjacent the left ventricle. In addition, electrodes 28 can also be carried by the housing of ICD 10.

Electrodes 28 are used to sense electrical activity of the heart, as well as to deliver pacing pulses or cardioversion/defibrillation shocks to the heart. Switch matrix 26 connects different electrodes to different components of ICD 10 depending on the sensing or therapy delivery function required.

Defibrillator circuitry 22 delivers high voltage shocks to the heart under the control of master control 16. The shocks are provided from defibrillation circuitry 22 through switch matrix 26 to selected electrodes 28. Similarly, master control 16 provides control signals to pacing circuitry 24, to cause pacing pulses to be delivered through switch matrix 26 to selected electrodes 28 in order to deliver pacing therapy.

Although in the embodiment of ICD 10 shown in FIG. 1 electrodes 28 are used to provide signals representing cardiac activity, other forms of sensors may also be used to provide sense signals that are processed by one or more of signal processing channels 20a-20d.

Each of signal processing channels 20a-20d comprises a digital signal processing channel for receiving input signals, converting those signals to digital form, processing those digital signals, and delivering the results of the signal processing to master control 16. The use of digital signal processing channels 20a-20d has significant advantages. Because most of the signal processing occurs in the digital rather than the analog realm, the same basic architecture and components can be used to provide a variety of different signal processing features. Changes in the signal processing can be made by changing instructions to master control 16, which in turn controls digital signal processor 36, rather than requiring redesign or replacement of analog components or circuits. In addition, the use of digital signal processing offers the potential of using high density digital integrated circuitry to implement signal processing functions.

As illustrated the input signal received by preamplifier 32 is an analog signal, which must be converted to digital form in order to perform digital signal processing functions. Preamplifier 32 is, in this embodiment, a variable gain preamplifier, although other types of preamplifier circuits may be used in other embodiments. Alternatively, preamplifier 32 could be omitted entirely in embodiments where electrodes 28 and/or switch matrix 26 are adapted to provide appropriate signals directly for conversion to digital form. Master control 16 provides control settings to preamplifier 32 to select the appropriate gain for that particular signal channel.

Sigma-delta ADC 34 receives the output of preamplifier 32 and converts the analog signal at its input to a digital value that is then provided to digital signal processor 36. Sigma-delta ADC 34 also receives the master clock MCLK signal from clock circuitry 16. Sigma-delta ADC 34 divides master clock MCLK to an appropriate conversion clock (CCLK) rate to perform sigma-delta analog-to-digital conversion. Typically, conversion clock CCLK has a number of different phases that are used within sigma-delta ADC 34 in the conversion process.

Sigma-delta ADC 34 can make use of a single stage or multiple stages of integration in the conversion process, and can provide a digital output in a single-bit or a multi-bit form. An advantage of sigma-delta ADC 34 is a relatively low energy consumption in the conversion process.

The output of sigma-delta ADC 34 is a multi-bit digital signal representing a sample value of the analog input signal at the sample rate of ADC 34. Digital signal processor 36 digitally filters the signal and senses an event, such as crossing of a threshold, to collect a series of samples over a time window. Digital signal processor 36 performs waveform analysis of the signal captured in the time window in order to identify the cardiac event within the time window. As part of this waveform analysis, digital signal processor 36 identifies the event based upon signal morphology. Form parameters are derived from the input signal waveform and are used to identify the cardiac event within the time window.

An input signal from an atrial electrode may contain both a P-wave signal representative of an atrial sinus event, and a Far Field R-wave signal representative of a ventricular event. Digital signal processor 36 must distinguish between a P-wave signal and a Far Field R-wave signal. In general, the P-wave signal represents the signal component of interest, and the Far Field R-wave signal represents cross talk or noise. In general, a P-wave has a different signal morphology from a Far Field R-wave signal. Therefore, form parameters derived from the atrial input signal within the time window can be used to determine whether the event sensed is a P-wave signal or a Far Field R-wave signal.

A more complicated situation occurs, however, when the P-wave and R-wave signals occur close in time to each other. The resulting signal within the time window may be the result of overlapping P-wave and Far Field R-wave signals. The result is a distorted waveform morphology that may not resemble either a P-wave signal or a Far Field R-wave signal.

In some cases, the Far Field R-wave may even lead the P-wave, so that the event time window triggered by a threshold crossing may not be an accurate indication of when the P-wave occurred. In order to identify P-waves within an atrial signal, digital signal processor 36 must be able to handle situations where the P-wave and Far Field R-wave signals may be overlapping.

Digital signal processor 36 includes a form parameter forecaster, which uses form parameters of composite waveforms created by superimposing templates of P-wave and Far Field R-wave signals at different time delays (i.e., different amounts of overlap). The form parameter forecaster enables digital signal processor 36 to identify a P-wave within the time window, and to determine its location within the time window. With the use of the form parameter forecaster, digital signal processor 36 is able to identify a P-wave even when the atrial input signal is distorted because the P-wave and Far Field R-wave events occur so close in time that their signal components are superimposed.

Figure 2A:
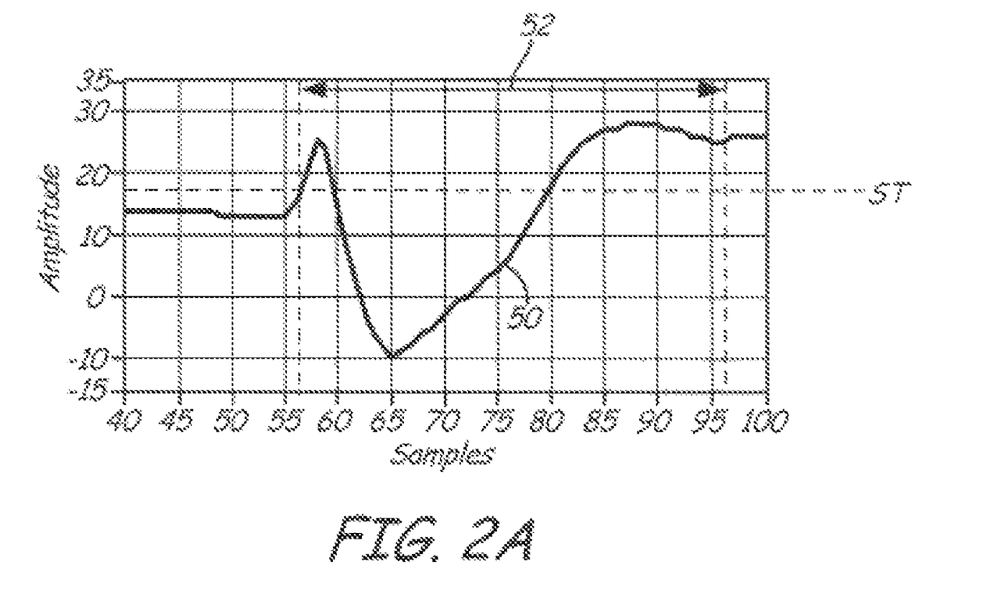
FIGS. 2A and 2B shows electrogram signals from an atrial electrode showing a P-wave and a Far Field R-wave, respectively.

FIGS. 2A and 2B show electrogram signals from an atrial electrode. FIG. 2A shows P-wave signal 50, which triggers sampling during time window 52 when P-wave signal crosses sensing threshold ST. The length of window 52 is shown as 40 samples in FIG. 2A.

Figure 2B:
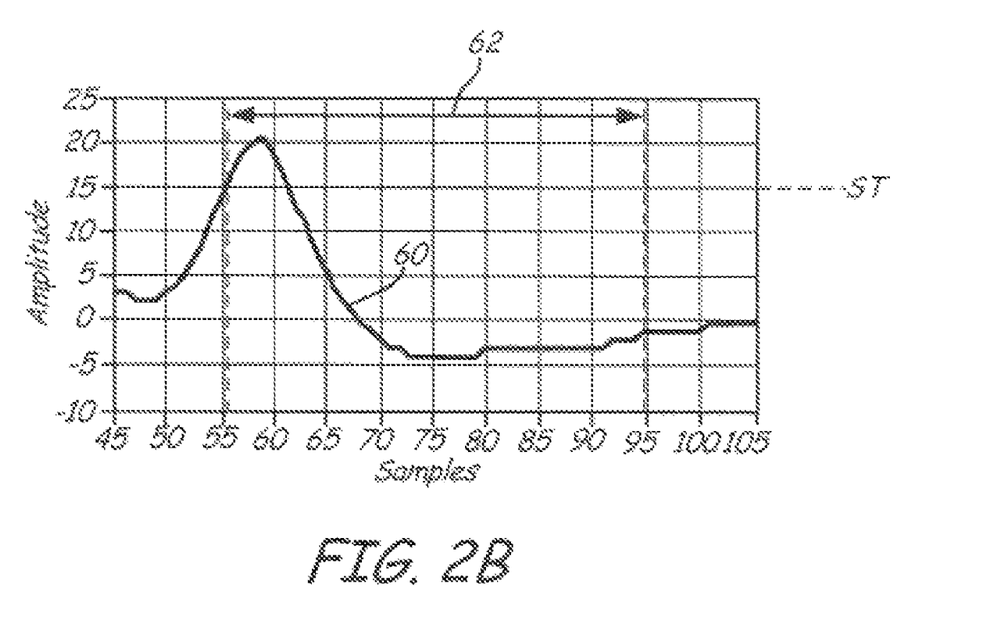

Far Field R-wave (FFRW) signal 60 is shown in FIG. 2B. FFRW signal 60 triggers sampling during time window 62 when it crosses sensing threshold ST. The length of window 62 is also 40 samples.

As can be seen from FIGS. 2A and 2B, P-wave signal 50 and FFRW signal 60 have different signal morphology. Form parameters can be derived from P-wave signal 50 and FFRW signal 60 and used to identify and distinguish these signals from one another. The form parameters can include, for example, some or all of the following: minimum voltage unfiltered signal (MiU); maximum voltage unfiltered signal (MaU); minimum voltage filtered signal (MiF); maximum voltage filtered signal (MaF); minimum voltage slope signal (MiS); maximum voltage slope signal (MaS); timestamp minimum voltage unfiltered signal (TMiU); timestamp maximum voltage unfiltered signal (TMaU); timestamp minimum voltage filtered signal (TMiF); timestamp maximum voltage filtered signal (TMaF); timestamp minimum voltage slope signal (TMiS); timestamp maximum voltage slope signal (TMaS); and signalwidth (time between the first and the last threshold-crossing).

Although FIGS. 2A and 2B show time windows of equal length resulting from a fixed number of samples following an event trigger, the end of the time window can also be determined by other factors, such as when the signal is returned to baseline (i.e., when the P-wave or Far Field R-wave has ended). This can result in time windows of different length for different signal types.

Digital signal processor 36 includes a form parameter forecaster in order to identify the P-wave even in those cases where the P-wave and the Far Field R-wave signals overlap in time (i.e., fall at least partially within the same event time window).

The form parameter forecaster feature of digital signal processor 36 makes use of templates representing a P-wave signal and a Far Field R-wave signal. The templates may each represent a single example of a signal collected when the P-wave and the Far Field R-wave signals are not overlapping. Alternatively, they may represent an average waveform created from multiple P-wave signals or multiple Far Field R-wave signals.

The form parameter forecaster makes use of composite waveforms created by superimposing the P-wave template and the FFRW template with different amounts of time shifting (i.e., different amounts of overlapping). For example, a set of composite waveforms can be created by shifting FFRW signal 60 into the window for P-wave signal 50 one sample at a time. The shifting can start, for example, with the first sample of signal 60 overlapping with the last sample of signal 50. The next composite waveform would then be created by overlapping the first two samples of signal 60 with the last two samples of signal 50. The process continues with different time shifts until FFRW signal 60 has been shifted entirely through P-wave signal 50. The set of composite waveforms will include a waveform representing a P-wave signal with no overlapping (i.e., the P-wave template), and a waveform representing an FFRW signal with no overlapping (i.e., the FFRW template).

Figure 3A:
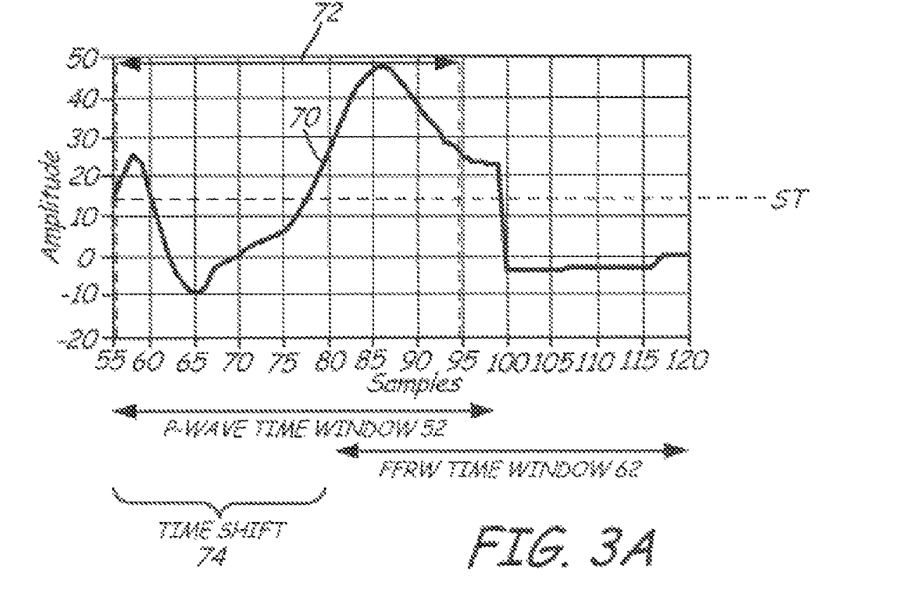
FIG. 3A shows a composite waveform produced by superimposing the waveforms of FIGS. 2A and 2B with a time shift, where the P-wave leads the Far Field R-wave.

FIGS. 3A and 3B show two examples of composite waveforms created by superimposing P-wave signal 50 and FFRW signal 60 by different amounts. In FIG. 3A, FFRW signal 60 is partially shifted into P-wave signal 50 to create composite waveform 70. Time shift 74 represents the number of samples (or amount of time) between the beginning of P-wave time window 52 and the beginning of FFRW time window 62. The shape of composite waveform 70 within the composite time window 72 represents a composite of P-wave signal 50 with a portion of FFRW signal 60.

Figure 3B:
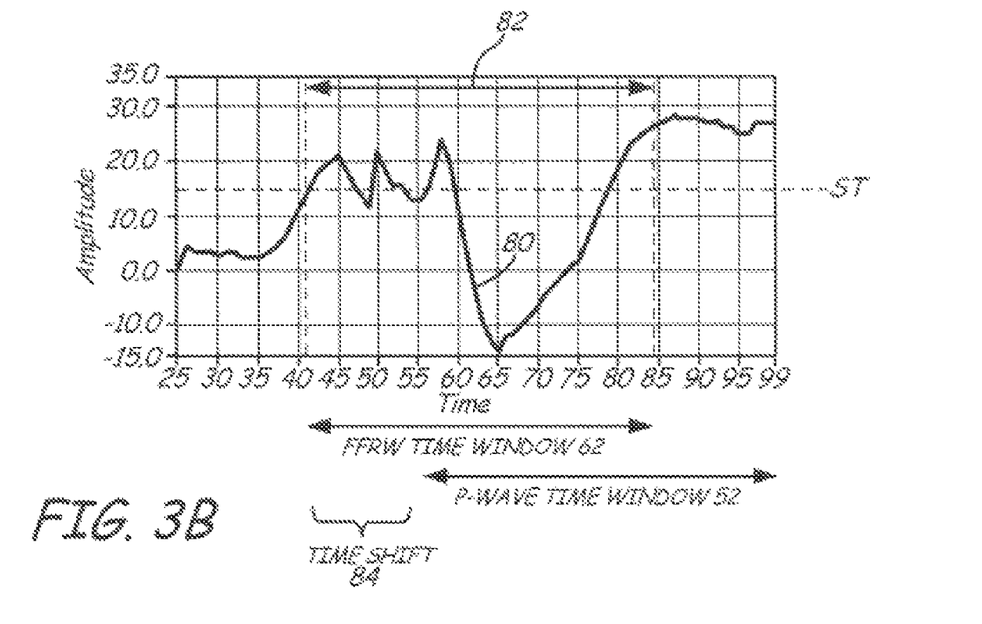
FIG. 3B shows a composite waveform produced by superimposing the waveforms of FIGS. 2A and 2B with a time shift, where the Far Field R-wave leads the P-wave.

FIG. 3B shows composite waveform 80, which shows a situation in which FFRW signal 60 is actually shifted with respect to P-wave signal 50 so that the start of time window 82 is based upon the beginning of FFRW time window 62 rather than the beginning of P-wave time window 52. Time shift 84 shown in FIG. 3B represents the delay by which P-wave signal 50 trails FFRW signal 60 within composite window 82. This time shift, which is referred to as the Superimposed Sense Compensation time, can be used by the form parameter forecaster to identify the location of P-wave signal 50 within composite waveform 80.

Digital signal processor 36 derives form parameters for each composite waveform, including the P-wave and FFRW templates that represent zero overlap. In order to identify each waveform uniquely, at least two form parameters should be used.

Figure 4:
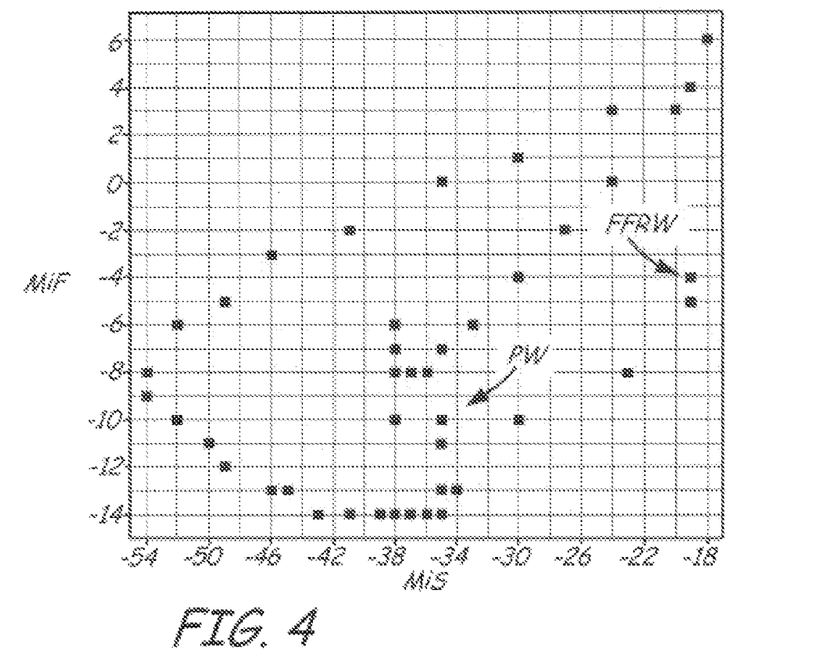
FIG. 4 shows a graph representing a set of two form parameters for each composite waveform.

For illustration, FIG. 4 shows a graph of two form parameters, with each data point representing a pair of form parameters for a different composite waveform. Included in the graph of FIG. 4 are data points labeled PW and FFRW. These two data points represent the pair of form parameters derived from the templates of P-wave signal 50 and FFRW signal 60 respectively. In the particular example shown in FIG. 4, the form parameter minimum voltage slope signal (MiS) is plotted along the horizontal axis. The form parameter minimum voltage filtered signal (MiF) is plotted along the vertical axis.

As shown in FIG. 2A, the minimum voltage of P-wave signal 50 within time window 52, MiF, is −10 millivolts. The minimum slope (i.e., the largest negative slope), MiS is about −35. Those values correspond to data point PW in FIG. 4.

Similarly, the minimum filtered voltage of FFRW signal 60, MiF, is about −4 millivolts. The minimum slope value, MiS, is about −19. These values correspond to the coordinates of data point FFRW in FIG. 4.

Figure 5:
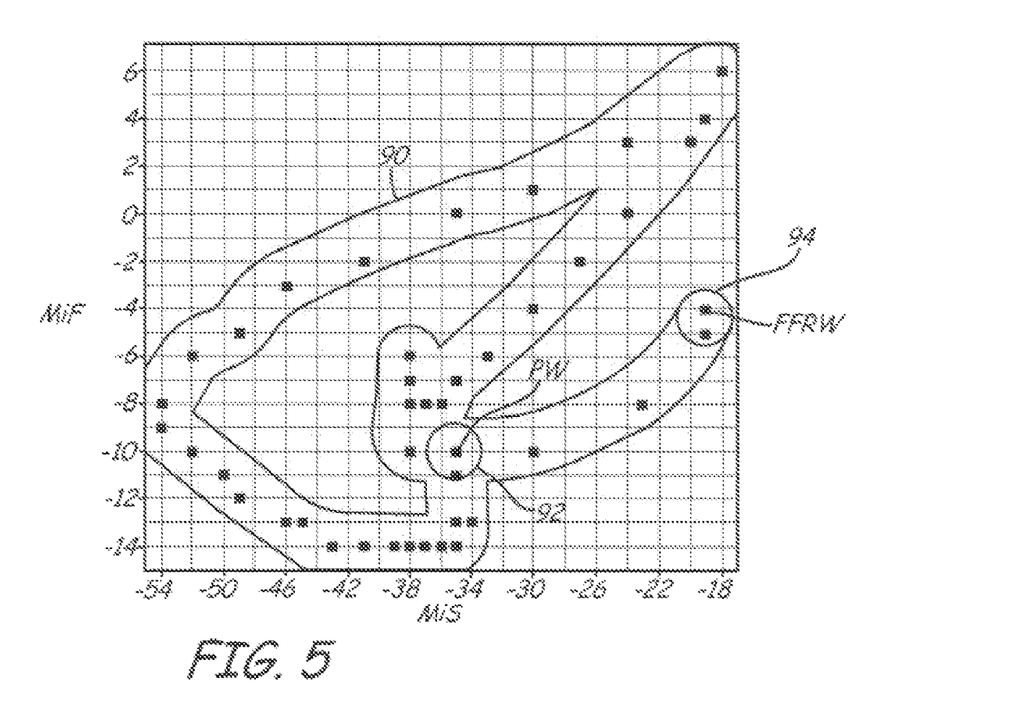
FIG. 5 is a graph of two form parameters with boundaries mapping a form parameter space.

Digital signal processor 36 then takes the form parameters for the composite waveforms, and creates form parameter boundaries around those data points. As illustrated in FIG. 5, boundaries 90 provide an outer limit within which form parameters of any signal including a P-wave, a Far Field R-wave, or a combination of the two should fall. Circle 92 represents a boundary of form parameters for events that will be classified as a P-wave only. Similarly, circle 94 represents coordinates that will be identified as a Far Field R-wave only. For those signals that produce a set of form factors that fall within boundaries 90, but not within circles 92 or 94, the signal is classified as a superimposed wave. Those signals having a set of form factors outside boundaries 90 are classified as "other".

The difference between the timestamp of an actual P-wave signal 50 is shown in FIG. 2A and the timestamp of a superimposed event can be used to determine the time of occurrence of a P-wave when a combined event (e.g., P-wave plus Far Field R-wave) is sensed. For those composite waveforms (like waveform 70 shown in FIG. 3A) where the Far Field R-wave is shifted only partially into the P-wave, the timestamp or trigger of the composite waveform will also be the same as the trigger or timestamp for the P-wave in that composite waveform. However, with those situations (like waveform 80 shown in FIG. 3B) where the Far Field R-wave has been shifted to where it leads the P-wave, the P-wave trails the beginning of the window, and a time adjustment using the Superposition Sense Compensation time is made to identify the proper location of the P-wave within the window.

Figure 6:
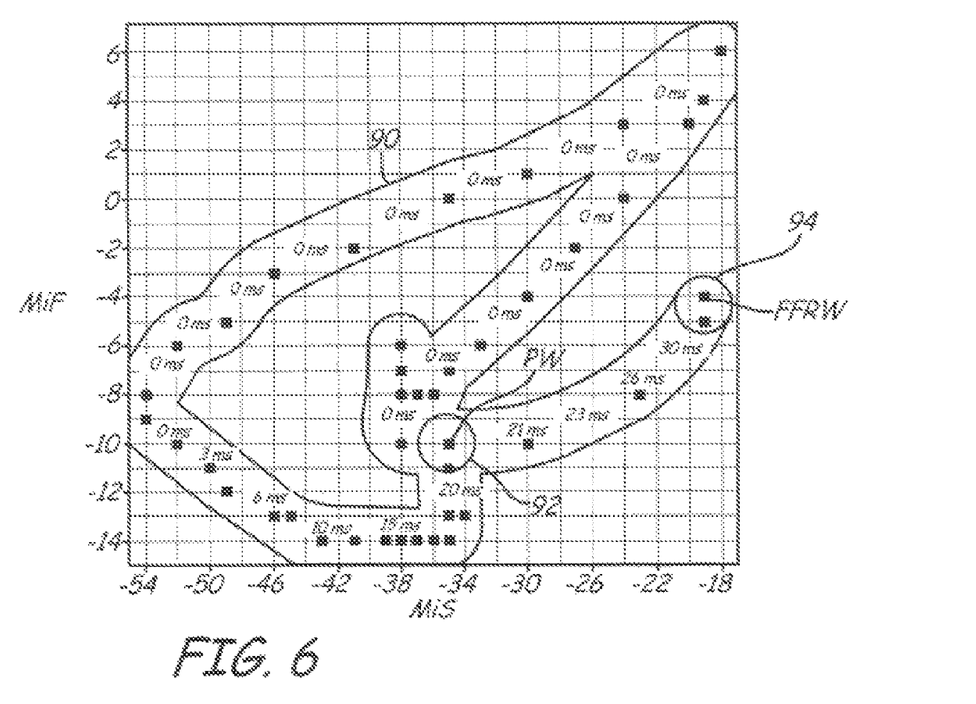
FIG. 6 shows a graph of two form parameters with boundaries and associated superposition sense compensation times.

FIG. 6 shows a graph similar to FIG. 5, but with a Superposition Sense Compensation time value added to indicate the amount of time delay between the beginning of the signal window and occurrence of the P-wave. An association of boundaries and form parameter sets with Superposition Sense Compensation times can be used by digital signal processor 36 to provide the timing of the P-wave within the time window of a sensed atrial event.

When digital signal processor 36 senses a threshold crossing (i.e., an atrial event), it triggers the creation of a new time window. Form parameters are derived from the input waveform sampled during the time window, and a comparison is made between the set of form parameters for the input waveform and the boundaries defined by the sets of waveform parameters mapped by the form parameter forecaster. Digital signal processor 36 compares the set of waveform parameters to the boundaries and determines whether the input signal represents a P-wave, an R-wave, a composite of the two, or a waveform that does not fall into any of those categories. If the input waveform is a composite of a P-wave and a Far Field R-wave signal, a determination is made of which composite waveform it most closely matches based on where the set of form parameters fall within the boundaries. A Superposition Sense Compensation time value (like those shown in FIG. 6) is associated with the input waveform based on the location within the boundaries.

Figure 7:
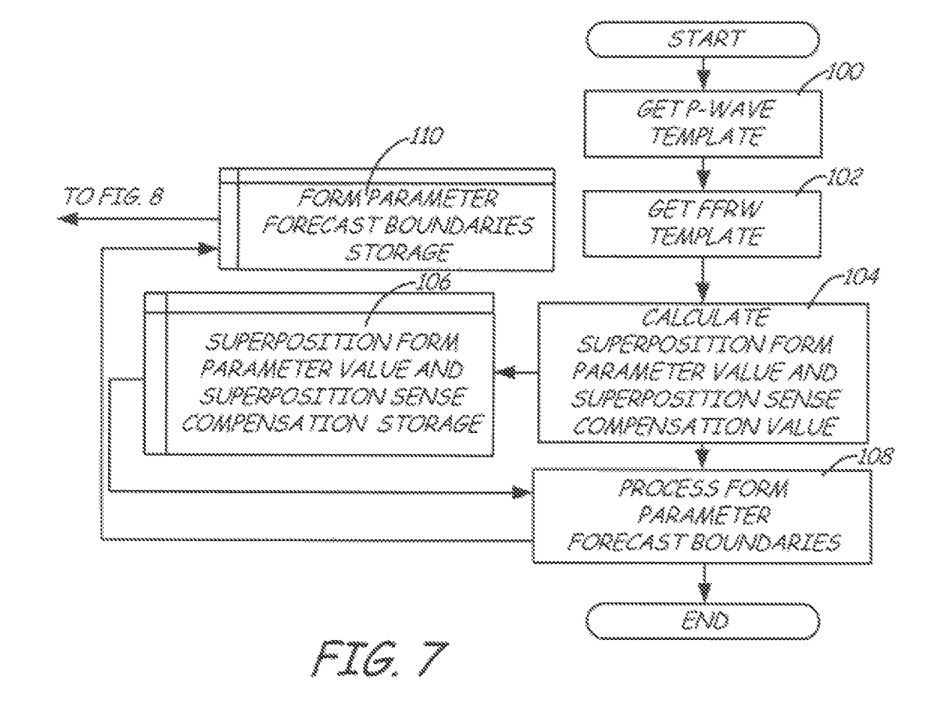
FIG. 7 is a flow diagram showing calculation of form parameter forecast boundaries.

FIG. 7 shows a flow diagram illustrating a process by which composite waveforms are created and used to produce form parameter forecast boundaries. The process begins by producing a waveform template of a first sensed event, such as a P-wave (step 100), and a waveform template of a second sensed event (i.e., a Far Field R-wave) (step 102). Each sensed event represents a window that has been triggered by the crossing of a sensing threshold signaling the beginning of the sensed event. The template may be a single waveform, or may be the result of averaging of similar waveforms collected over a period of time. Each template should be representative of a window that contains only that sensed event, and not a time window in which the two events are so closely spaced that they both occur within the window.

At step 104, both waveform templates are used to calculate a superimposed or composite waveform with a particular time shift or degree of overlap. Form parameters are derived from the composite waveform. The set of form parameter values and a calculated Superposition Sense Compensation value related to the time shift are stored in memory (step 106). The creation of composite waveforms and the calculation of form parameter value sets and Superposition Sense Compensation values is repeated until all of the possible composite waveforms have been created and values have been stored.

The stored form parameter sets and Superposition Sense Compensation values are then used to determine form parameter forecast boundaries. The form parameter forecast boundaries, and associated Superposition Sense Compensation values are stored in memory (step 110).

Figure 8:
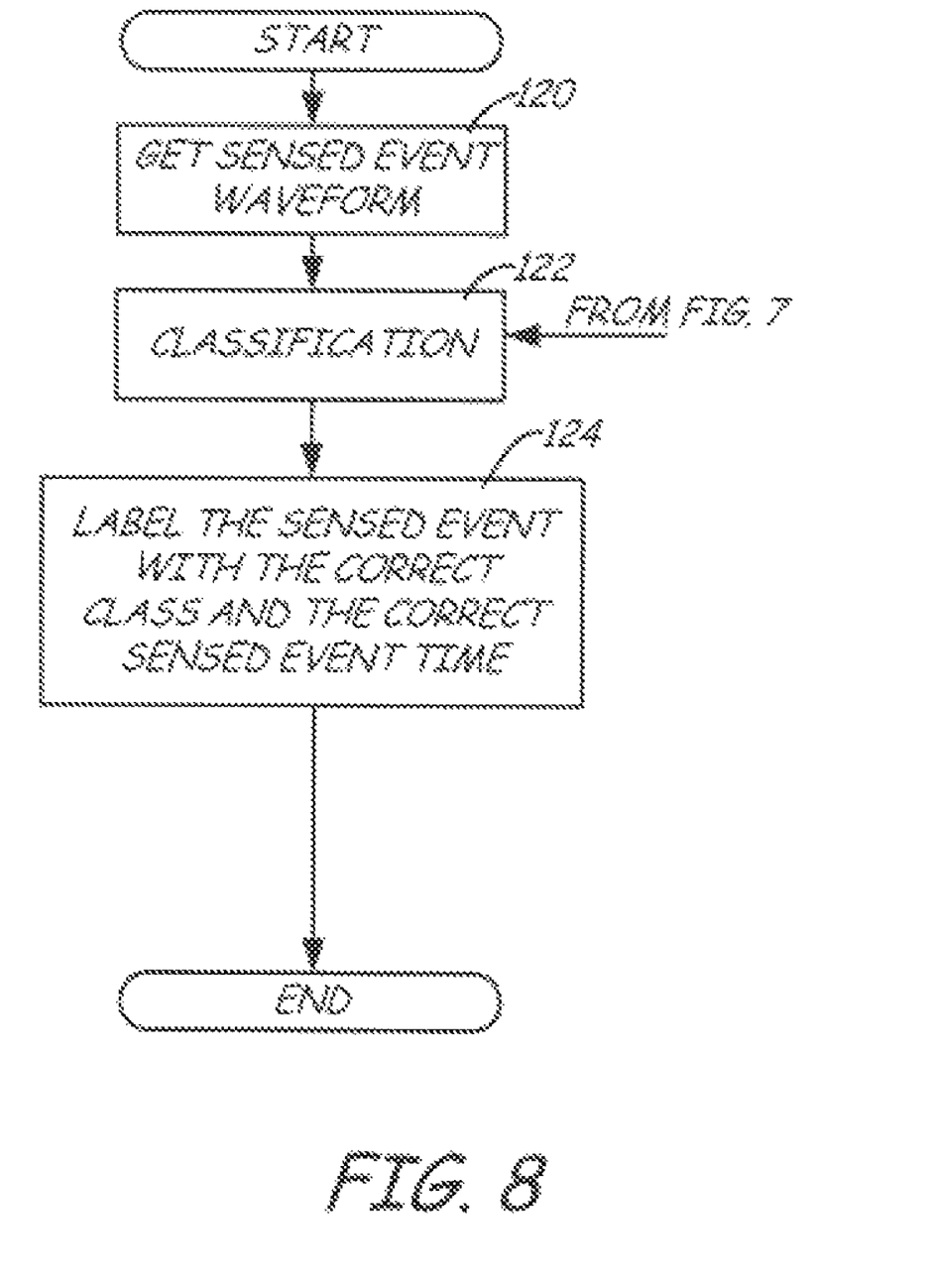
FIG. 8 shows a flow diagram showing classification of incoming input signal events using the form parameter forecast boundaries produced by the process shown in FIG. 7.

FIG. 8 shows a process used for classifying incoming sensed events. As digital signal processor 36 receives an incoming digitized waveform from analog-to-digital converter 34, it filters the incoming signal and compares the signal to a sensing threshold. When a sensed event occurs, a window is triggered by the event to capture the input signal over a window length of, for example, 40 samples. (Step 120). The input waveform is then analyzed to derive a set of form parameters similar to the form parameters derived from the waveform templates and the composite waveforms. Based upon the form parameter set, the input waveform is classified using the form parameter forecast boundaries stored in memory (step 122).

The sensed event may have form parameters that fall within the forecast boundaries and may be classified as a P-wave, a Far Field R-wave, a superimposed signal or other. In those cases where the sensed event does not fall within the form parameter forecast boundaries and is classified as "other", further processing of the input waveform may be performed by digital signal processor 36 using other signal processing procedures.

The input waveform is labeled with its correct class based upon the form parameter forecast boundaries. Depending upon where the parameters of the input waveform were located within the forecast boundaries, a Superposition Sense Compensation time may be used to provide a correct sensed event time for the P-wave. (Step 124).

With use of the form parameter forecaster, digital signal processor 36 is able to identify and distinguish P-wave signals and Far Field R-wave signals, even when the signals occur so close in time that they overlap one another and result in a distorted input signal. The same process can be used with other physiologic signals, and with other signal components that may overlap and thus distort a signal during a triggered event time window.

For simplicity of discussion and illustration, an example has been provided using only two form parameters. This has allowed a relatively simple graphical illustration in two dimensions of form parameter boundaries. The form parameter forecaster, however, can use more than two form parameters derived from each waveform, rather than only two as described. The use of a larger number of form parameters can provide greater discrimination between different waveforms based upon their morphology.

Similarly, the form parameter forecaster has been described in the context of composites of two signals of known shape. It can, however, be extended to situations involving more than two signals.

Although the present invention has been described with reference to preferred embodiments, workers skilled in the art will recognize that changes may be made in form and detail without departing from the spirit and scope of the invention.

The invention claimed is:

1. A signal processing channel for identifying events in an analog input signal, the signal processing channel comprising:

an analog-to-digital converter programmed to convert the analog input signal to a digital waveform, wherein the analog input signal has a first signal and a second signal overlapping in time; and a digital processor programmed to analyze a segment of the digital waveform, the segment has the first signal and the second signal overlapping in time during a time window triggered by an event, the digital processor including a form parameter forecaster that provides forecasted form parameters based upon different superpositions of a first signal component and a second signal component, the digital processor identifying the first signal component in the time window based upon a set of form parameters derived from the segment of the digital waveform during the time window and the forecasted form parameters, wherein the different superpositions correspond to a plurality of different amounts of overlap of the first signal component and the second signal component and wherein the first signal and second signal are physiologic signals and the first signal component and second signal component are physiologic signal components.

2. The signal processing channel of claim 1, wherein the form parameter forecaster derives a set of form parameters for each of the different superpositions of the first signal component and the second signal component, and defines form parameter boundaries representative of the forecasted form parameters.

3. The signal processing channel of claim 2, wherein the digital processor identifies the event as containing the first signal component based upon a comparison of the set of form parameters derived from the segment of the digital waveform during the time window with the form parameter boundaries.

4. The signal processing channel of claim 3, wherein the form parameter associates superposition sense compensation time values with different regions within the form parameter boundaries.

5. The signal processing channel of claim 4, wherein the superposition sense compensation time represents a time by which the second signal component leads the first signal component in a superposition of the first and second signal components.

6. The signal processing channel of claim 5, wherein the digital processor identifies a location of the first signal component in the time window based upon the superimposed sense compensation time for the region within the form parameter boundaries corresponding to the set of form parameters derived from the segment of the digital waveform during the time window.

7. The signal processing channel of claim 1, wherein the form parameter forecaster:
 generates a first waveform template representative of the first signal component;
 generates a second waveform template representative of the second signal component;
 generates a plurality of composite waveforms, each representing a superposition of the first waveform template and the second waveform template with a different relative time shifts wherein the different relative time shifts represent the different amounts of overlap of the first signal component and the second signal component; and
 derives a set of form parameters from each composite waveform.

8. The signal processing channel of claim 7, wherein the form parameter forecaster:
 derives a multidimensional map of the sets of form parameters of the composite waveforms; and
 defines form parameter boundaries based upon the map.

9. The signal processing channel of claim 1, wherein the input signal comprises a physiologic signal, the first signal component comprises a signal representative of a physiologic event, and the second signal component comprises cross talk.

10. The signal processing channel of claim 9, wherein the physiologic signal comprises a sensed atrial signal, the first signal component comprises a P-wave signal, and the second signal component comprises a Far Field R-wave signal.

11. An implantable medical device comprising:
 a sensor for producing an input signal having a first signal and a second signal overlapping in time; and
 a signal processor programmed to analyze an event waveform of the input signal during a sensed event by comparing a set of waveform parameters derived from the event waveform with forecasted waveform parameters of different superpositions of the first and second signals, and identifying whether the event waveform contains one or both of the first and second signals based upon the, wherein the different superpositions correspond to a plurality of different amounts of overlap of the first signal and the second signal and the first signal and the second signal are physiologic signals.

12. The implantable medical device of claim 11, wherein the input signal comprises an atrial signal, the first signal comprises a P-wave, and the second signal comprises a Far Field R-wave.

13. The implantable medical device of claim 12, wherein the signal processor provides a location of the P-wave within the event waveform based upon the comparison.

14. The implantable medical device of claim 11, wherein the sensed event comprises a time window triggered by a crossing of a sensing threshold by the input signal.

15. The implantable medical device of claim 11, wherein the signal processor generates composite waveforms representing different superpositions of waveform templates representing the first and second signals, and derives a set of form parameters from each composite waveform.

16. The implantable medical device of claim 15, wherein the signal processor derives form parameter boundaries from a mapping of the sets of form parameters of the composite waveforms.

17. The implantable medical device of claim 16, wherein the signal processor associates a superposition sense compensation time with different regions within the form parameter boundaries.

18. The implantable medical device of claim 17, wherein the signal processor identifies a location of the first signal in the event waveform based upon the superposition sense compensation time for the region in which the set of form parameters of the event waveform are located.

* * * * *